United States Patent [19]

Keeton

[11] Patent Number: 4,967,914

[45] Date of Patent: Nov. 6, 1990

[54] SHARP INSTRUMENT HOLDER FOR OPERATING ROOMS

[76] Inventor: William F. Keeton, 135 Woodchase Ct., Atlanta, Ga. 30319

[21] Appl. No.: 415,853

[22] Filed: Oct. 2, 1989

[51] Int. Cl.⁵ .................................................. A47F 7/00
[52] U.S. Cl. ..................................... 211/70.7; 211/126
[58] Field of Search ............... 211/70.7, 126; 206/370, 206/369, 363, 373; 248/37.3

[56] References Cited

U.S. PATENT DOCUMENTS

| | | | |
|---|---|---|---|
| 72,009 | 12/1867 | Foster | 248/37.3 |
| 1,886,075 | 11/1932 | Zorsch | 211/70.7 |
| 2,664,005 | 12/1953 | Kosinski | 211/70.7 X |
| 2,903,129 | 9/1959 | Anderson, III | 206/363 |
| 4,229,420 | 10/1980 | Smith et al. | 206/370 X |
| 4,626,971 | 12/1986 | Schultz | 206/370 X |

*Primary Examiner*—Blair M. Johnson
*Attorney, Agent, or Firm*—James B. Middleton

[57] ABSTRACT

An instrument holder receives sharp instruments used in the operating room, and both supports the instruments for easy retrieval when needed and protects the staff from accidentally engaging the sharp portion of the instruments. The holder has an instrument support flange to hold the instruments, and a closed housing that receives the sharp portion of the instruments to guard the sharp portions. The instrument holder is held in place by a pressure sensitive adhesive.

4 Claims, 1 Drawing Sheet

U.S. Patent    Nov. 6, 1990    4,967,914
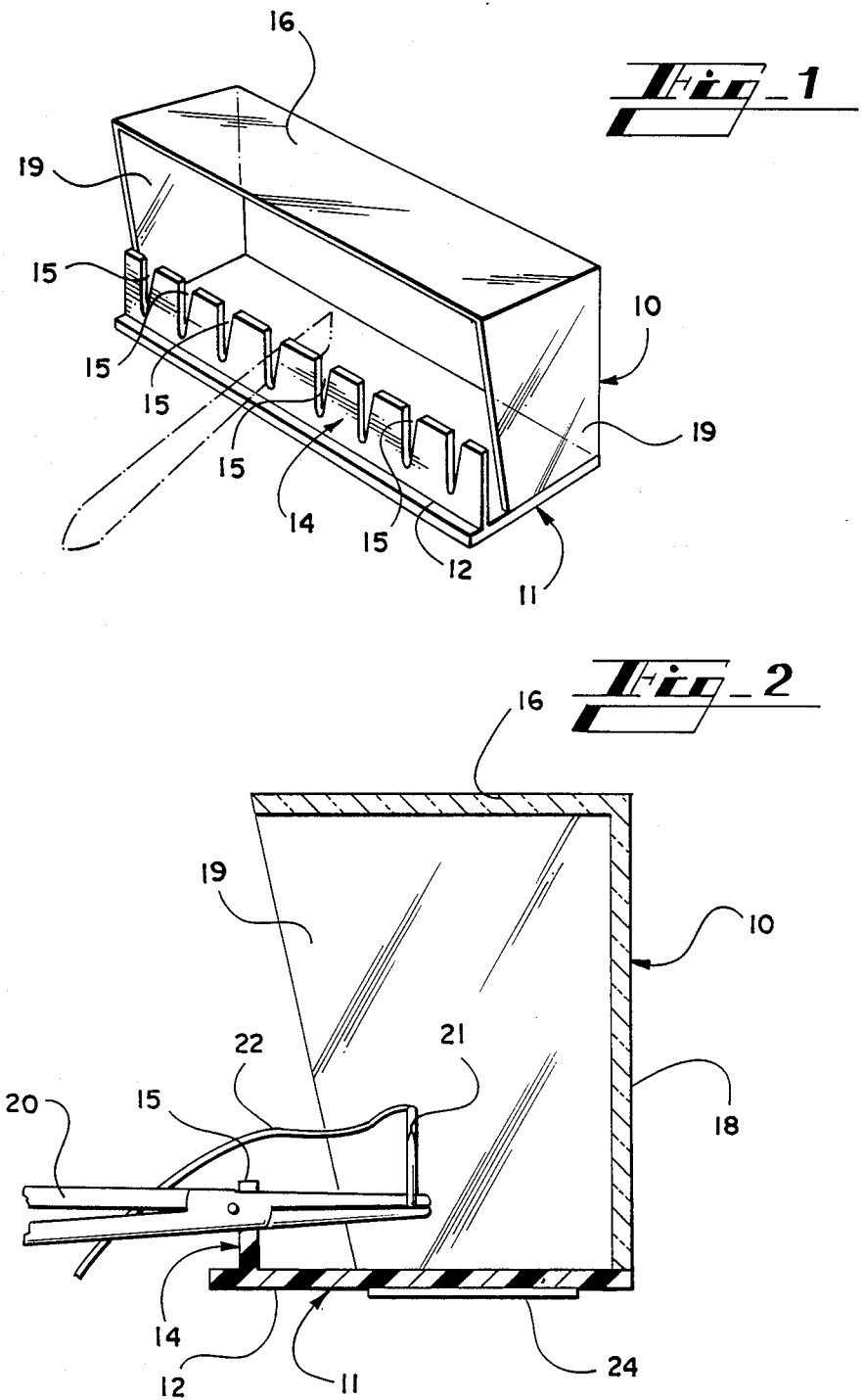

SHARP INSTRUMENT HOLDER FOR OPERATING ROOMS

INFORMATION DISCLOSURE STATEMENT

A modern operating room can be hazardous in that the people involved must utilize very sharp instruments. While the possibility of physical injury is undesirable, the operating room is an especially hazardous environment in that many diseases might be prevalent so that an injury might simultaneously infect a person with a disease.

Part of the real hazard in an operating room is brought about by the fact that one or more surgeons are operating on a patient, and their attention is directed primarily to the patient rather than to other matters in the operating room. It is therefore relatively easy for a surgeon, or an assistant, to be injured simply in reaching for a particular tool or device that the surgeon needs. An obvious solution to the problem might be to encase the sharp instruments to prevent damage, and indeed there have been knives having guards thereover. Such a solution renders the knife somewhat more difficult for the surgeon to use, and the solution is not applicable to all sharp instruments.

SUMMARY OF THE INVENTION

This invention relates generally to instrument holders, and is more particularly concerned with the holder for sharp instruments where by the sharp portion of the instrument is guarded against inadvertent contact.

The present invention provides a protective housing for receiving the sharp portion of a surgical instrument. An instrument support is mounted adjacent to the housing for supporting the instrument while the sharp portion is received within the housing. The arrangement is such that the handle of the instrument is then available to be easily grasped by the surgeon or an assistant while engagement with the sharp portion of the instrument is prevented.

It is contemplated that the upper portion of the housing will be substantially transparent to assist in selecting the desired instrument. Also, means may be provided for holding the device in the desired location.

BRIEF DESCRIPTION OF THE DRAWINGS

These and other features and advantages of the present invention will become apparent from consideration of the following specification when taken in conjunction with the accompanying drawings in which:

FIG. 1 is a perspective view showing one form of instrument holder made in accordance with the present invention, and showing a scalpel in phantom; and, FIG. 2 is a transverse cross-sectional view through the device of FIG. 1, and showing a clamp having a needle therein.

DETAILED DESCRIPTION OF THE EMBODIMENT

Referring now more particularly to the drawings, to that embodiment of the invention here presented by way of illustration, FIG. 1 illustrates a housing generally designated at 10, the housing 10 being received on a base 11, the base 11 protruding forwardly beyond the housing 10 to provide a shelf 12. Extending upwardly from the shelf 12, there is an instrument support designated at 14. It will be noted that the instrument support 14 defines a plurality of instrument receiving notches 15.

It will be observed that the housing 10 is generally transparent. With the housing 10 made of transparent material, the top 16 extends forwardly, to be somewhat above the shelf 12. This arrangement provides a great degree of protection in that it will be very difficult for a person to contact the sharp portion of an instrument inadvertently. It will be understood, however, that the housing 10 may be constructed of materials that are not transparent, such as stainless steel. In this event, it may be desirable to shorten the top 16 of the housing 10 to provide better visibility of the various instruments for easier selection of the desired instrument.

The arrangement of the present invention is well shown in FIG. 2 of the drawings where it will be seen that the housing 10 includes a generally vertical rear wall 18 and end walls 19. As here shown, the rear wall 18, the end walls 19 and the top wall 16 are made of transparent material. The base 11 is indicated as being made of a plastic material. Those skilled in the art will realize that the sharp instrument holder of the present invention can be constructed of many different materials, but the use of polymeric resins will render the device quite inexpensive to manufacture so that the device can be treated as a disposable. With this construction, it will be understood that the base 11 can be made of a material having sufficient coloring or other fillers to render the material substantially opaque, and preferably relatively dark in color. The same material can be used for the rear wall 18, end walls 19 and top 16, but with the material left uncolored so that it is substantially transparent. While many different materials might be selected, it will be understood that acrylics such as methylmethocrylate would do extremely well, and less expensive materials such as styrene or polycarbonate can be used. Other materials will suggest themselves to those skilled in the art. Nevertheless, the instrument holder of the present invention can also be made of durable materials such as stainless steel so the device can be utilized as a permanent device, and sterilized between uses.

In FIG. 2 of the drawings, it will be seen that a clamp 20 is shown resting in one of the notches 15 of the instrument receiver 14. The jaws of the clamp 20 are holding a needle 21 having attached suture material 22. Such an arrangement is very common in operating rooms, and it would be seen that the point of the needle 21 is upstanding so it would be extremely easy for a person to engage the point of the needle accidentally. Using the sharp instrument holder of the present invention, it will be seen that the clamp 20 is held in position for easy selection by a surgeon or an assistant, while the needle 21 is safely guarded by the housing 10, and it would be very difficult for a person engage the needle 21 accidentally.

Also shown in FIG. 2, there is an adhesive strip designated at 24. It is contemplated that the adhesive strip 24 will be a strip of pressure sensitive adhesive with a release paper as is well known in the art. When the instrument holder is to be utilized, the release paper will be removed and the instrument holder will be adhered to the mayo stand or other convenient surface in the operating room. When the procedure is completed, the instrument holder can be readily removed and discarded.

In FIG. 1, the instrument holder is shown with a plurality of notches 15, and it is contemplated that a given instrument holder will have a sufficient number of notches 15 to receive the sharp instruments used during a given procedure. It may sometimes be desired to limit the instrument holder to the receipt of a single instrument, or to allow a large number of instruments to be received in the holder. All such variations are within the inventive concept of the present invention.

It will therefore be understood by those skilled in the art that the particular embodiment of the invention here presented is by way of illustration only, and is meant to be in no way restrictive; therefore, numerous changes and modifications may be made, and the full use of equivalents resorted to, without departing from the spirit or scope of the invention as outlined in the appended claims.

What is claimed is:

1. An instrument holder for use in an operating room in combination with at least one sharp instrument, said sharp instrument including a handle that is safe to grasp and a sharp portion that is unsafe to grasp, said instrument holder including an instrument supporting means for supporting said sharp instrument in a position such that said handle portion is easily grasped, and a housing for substantially enclosing said sharp portion for preventing inadvertent contact with said sharp portion, said instrument holder further including a base plate, said base plate defining a bottom for said housing, said base plate further defining a shelf extending forwardly from said housing for carrying said instrument supporting means, said instrument supporting means comprising a flange extending upwardly from said shelf, said flange defining at least one notch therein for receiving said handle of said sharp instrument.

2. An instrument holder as claimed in claim 1, said housing further including end walls extending upwardly from said base, and a top supported by said end walls, said top being transparent to allow viewing of said sharp portion of said instrument in said housing.

3. An instrument holder as claimed in claim 2, said housing further including a rear wall extending upwardly from said base plate, said base plate being generally opaque, said housing being generally transparent.

4. An instrument holder as claimed in claim 1, said housing further including end walls extending upwardly from said base, and a top supported by said end walls, and a rear wall extending upwardly from said base plate, said instrument holder being constructed of sterilizable material.

* * * * *